US011478270B2

(12) United States Patent
Carlson et al.

(10) Patent No.: US 11,478,270 B2
(45) Date of Patent: Oct. 25, 2022

(54) ATHERECTOMY MOTOR CONTROL SYSTEM

(71) Applicant: BOSTON SCIENTIFIC SCIMED, INC., Maple Grove, MN (US)

(72) Inventors: Corydon Carlson, Stillwater, MN (US); David Gordon Spangler, New Richmond, WI (US); Daniel Frank Massimini, Brooklyn Park, MN (US); Laszlo Trent Farago, Hudson, WI (US); Mark A. Hilse, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 332 days.

(21) Appl. No.: 16/284,708

(22) Filed: Feb. 25, 2019

(65) Prior Publication Data
US 2019/0262032 A1    Aug. 29, 2019

Related U.S. Application Data

(60) Provisional application No. 62/636,103, filed on Feb. 27, 2018.

(51) Int. Cl.
*A61B 17/3207* (2006.01)
*G05B 11/42* (2006.01)
(Continued)

(52) U.S. Cl.
CPC ...... *A61B 17/320758* (2013.01); *G05B 11/14* (2013.01); *G05B 11/42* (2013.01);
(Continued)

(58) Field of Classification Search
CPC ...... G05B 13/021; G05B 13/02; G05B 13/42; A61B 2017/00119; A61B 2017/00199; A61B 2017/00398; A61B 2218/007
See application file for complete search history.

(56) References Cited

U.S. PATENT DOCUMENTS

2007/0251939 A1* 11/2007 Minkovich ....... H01L 21/67225
219/505
2008/0146965 A1* 6/2008 Privitera ............ A61B 10/0266
600/567
(Continued)

FOREIGN PATENT DOCUMENTS

EP          2508141 A1     10/2012
EP          3053534 A1     8/2013
WO          0056230 A2     9/2000

OTHER PUBLICATIONS

"What is a PID Controller: Working & Its Applications, 2013, El-Pro-Cus, URL: https://www.elprocus.com/the-working-of-a-pid-controller/" (Year: 2013).*

(Continued)

*Primary Examiner* — Santosh R Poudel
(74) *Attorney, Agent, or Firm* — Seager, Tufte & Wickhem LLP

(57) ABSTRACT

An atherectomy system includes a drive mechanism that is adapted to rotatably actuate an atherectomy burr and a controller that is adapted to regulate operation of the drive mechanism. In some cases, the drive mechanism includes a drive cable that is coupled with the atherectomy burr and a drive motor that is adapted to rotate the drive cable. The controller is adapted to receive an indication of an increase in torque experienced at the atherectomy burr and is further adapted to, in response, regulate operation of the drive mechanism such that the increase in torque results in a noticeable reduction in speed of the drive mechanism such that a user of the atherectomy system notices the reduction in speed and is alerted to the increase in torque.

3 Claims, 9 Drawing Sheets

(51) Int. Cl.
  *G05B 13/02* (2006.01)
  *G05B 11/14* (2006.01)
  *A61B 17/00* (2006.01)
  *A61B 90/00* (2016.01)

(52) U.S. Cl.
  CPC .......... *G05B 13/02* (2013.01); *G05B 13/021* (2013.01); *A61B 2017/00017* (2013.01); *A61B 2017/00119* (2013.01); *A61B 2017/00199* (2013.01); *A61B 2017/00398* (2013.01); *A61B 2090/066* (2016.02); *A61B 2090/08021* (2016.02); *A61B 2218/002* (2013.01); *A61B 2218/007* (2013.01)

(56) References Cited

U.S. PATENT DOCUMENTS

| | | | |
|---|---|---|---|
| 2010/0125276 A1 | 5/2010 | Palermo | |
| 2011/0213391 A1* | 9/2011 | Rivers | A61B 17/320758 606/159 |
| 2012/0095461 A1* | 4/2012 | Herscher | A61B 18/1492 606/45 |
| 2015/0025538 A1* | 1/2015 | Kust | B25B 23/14 606/104 |
| 2015/0201956 A1* | 7/2015 | Higgins | A61B 17/3207 606/159 |

OTHER PUBLICATIONS

International Search Report and Written Opinion dated Apr. 26, 2019, for International Application No. PCT/US2019/019404.

* cited by examiner

ATHERECTOMY MOTOR CONTROL SYSTEM

CROSS-REFERENCE TO RELATED APPLICATIONS

This application claims the benefit of priority under 35 U.S.C. § 119 of U.S. Provisional Application No. 62/636,103, filed Feb. 27, 2018, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy system that includes a drive mechanism that is adapted to rotatably actuate an atherectomy burr and a controller that is adapted to regulate operation of the drive mechanism. The controller is adapted to receive an indication of an increase in torque experienced at the atherectomy burr and is further adapted to regulate operation of the drive mechanism such that the increase in torque results in a noticeable reduction in speed of the drive mechanism such that a user of the atherectomy system notices the reduction in speed and is alerted to the increase in torque.

Alternatively or additionally, the drive mechanism may include a drive cable that is coupled with the atherectomy burr and a drive motor that is adapted to rotate the drive cable.

Alternatively or additionally, if the atherectomy burr becomes stuck, the controller is further adapted to increase the torque provided by the drive mechanism until a torque threshold is reached and direct the drive mechanism to reverse in order to unwind energy in the drive mechanism.

Alternatively or additionally, the atherectomy system may further include a user interface operably coupled to the controller so that the controller is able to display information regarding performance of the drive mechanism.

Alternatively or additionally, the controller may be further adapted to regulate operation of the drive mechanism such that the reduction in speed is greater than would otherwise result from the increase in torque in order to alert the user to the increase in torque.

Alternatively or additionally, the controller may include a reference block that is adapted to receive a speed signal and output a reference signal, a control block that is adapted to receive the reference signal from the reference block and generate a resulting control effort signal and a drive circuit that is adapted to receive the control effort signal from the control block and regulate operation of the drive mechanism accordingly.

Alternatively or additionally, the control block may include a Proportional controller.

Alternatively or additionally, the control block may include a Proportional Integral Derivative (PID) controller.

Alternatively or additionally, the reference block may be adapted to output a reference signal that is either a nominal positive value, a small negative value or zero.

Alternatively or additionally, the reference block may be adapted to default to the nominal positive value for the reference signal upon startup of the atherectomy system.

Alternatively or additionally, the reference block may be adapted to add an offset value to the reference signal in order to accurately hold speed of the drive mechanism during a no-load situation.

Another example of the disclosure is an atherectomy system that includes a drive mechanism that is adapted to rotatably actuate an atherectomy burr and a control system that is adapted to regulate operation of the drive mechanism. The control system includes a reference block for determining a speed reference, the speed reference selectable between a nominal value, a negative value, and zero and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining an output signal for the drive mechanism. The PID controller is further adapted to add an offset value to the speed reference received from the reference block and is further adapted to provide a reduction in motor speed of the drive mechanism that is greater than what would otherwise normally occur in response to an increasing torque experienced at the atherectomy burr.

Alternatively or additionally, the I gain value and the D gain value may be set to zero or about zero.

Alternatively or additionally, the P gain value may be set to a low value.

Alternatively or additionally, the drive mechanism may include a drive cable that is coupled with the atherectomy burr and a drive motor that is adapted to rotate the drive cable.

Alternatively or additionally, in response to an increasing torque as a result of a stuck atherectomy burr, the PID controller may be adapted to increase torque until a predetermined threshold is reached and the reference block may be adapted to set the speed reference to the negative value in order to unwind energy stored in the drive mechanism.

Another example of the disclosure is an atherectomy system that includes a drive motor that is operably coupled to a drive cable and an atherectomy burr that is operably coupled to the drive cable. A control system is operably coupled to the drive motor and includes a feedback loop that is adapted to monitor performance of the drive motor and output a control effort signal and a drive circuit that is adapted to receive the control effort signal and regulate operation of the drive motor in accordance with the control effort signal. The control system is further adapted to provide a reduction in motor speed of the drive motor that is greater than what would otherwise normally occur in response to an increasing torque experienced at the atherectomy burr.

Alternatively or additionally, the feedback loop may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal.

Alternatively or additionally, the feedback loop may be adapted to add an offset value to the reference signal in order to accurately hold speed of the drive motor during a no-load situation.

Alternatively or additionally, if the atherectomy burr becomes stuck, the control system may be further adapted to increase the torque provided by the drive motor until a torque threshold is reached and to drive the drive motor in reverse in order to unwind energy in the drive cable.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
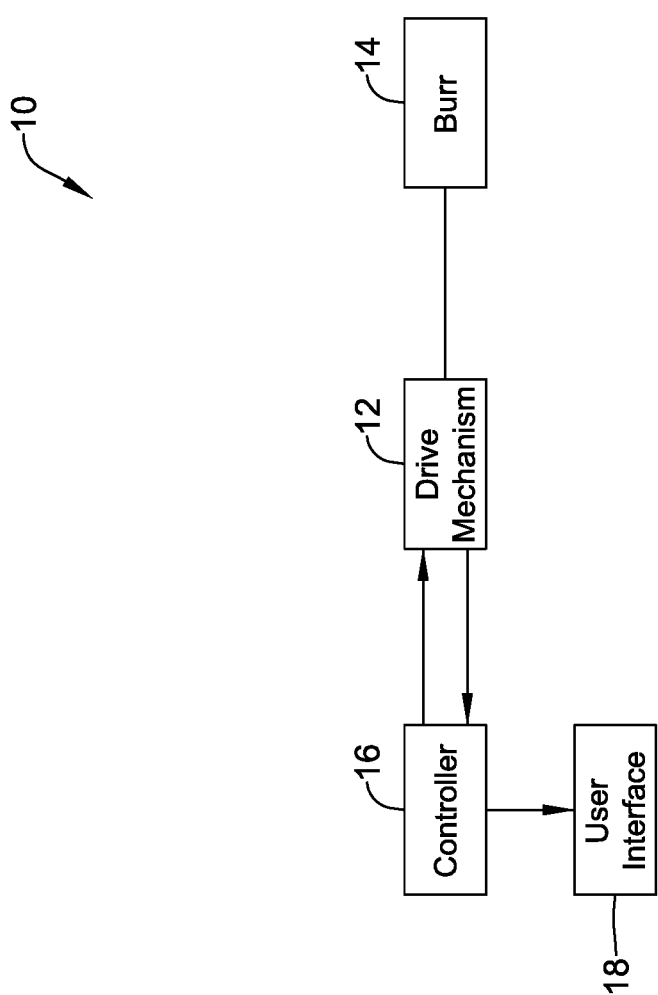
FIG. 1 is a schematic block diagram of an example atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 is a schematic block diagram of an example atherectomy system 10 that includes a drive mechanism 12 that is adapted to rotatably actuate an atherectomy burr 14. The atherectomy system 10 includes a controller 16 that is adapted to regulate operation of the drive mechanism 12. In some cases, the atherectomy system 10 may include a user interface 18 that may be operably coupled to the controller 16 such that the controller 16 is able to display information regarding the performance of the drive mechanism 12. This information may, for example, include one or more of a current speed of the drive mechanism 12, a current torque being experienced by the atherectomy burr 14, and the like. In some cases, the atherectomy burr 14 may also be referred to as being or including a cutting head or a cutting member, and these terms may be used interchangeably.

In some cases, for example, the controller 16 may be adapted to receive an indication of an increase in torque experienced at the atherectomy burr 14. In some cases, for example, an increase in torque may be realized by seeing a corresponding increase in the power consumption of the drive mechanism 12. The controller 16 may be further adapted to regulate operation of the drive mechanism 12 such that the increase in torque results in a noticeable reduction in speed of the drive mechanism such that a user of the atherectomy system 10 notices the reduction in speed and is alerted to the increase in torque. In some cases, the reduction in speed may be greater than what would otherwise be expected from the increased torque load on the drive mechanism 12.

In some cases, if for example the atherectomy burr 14 becomes stuck, the controller 16 may be further adapted to increase the torque provided by the drive mechanism 12 until a torque threshold is reached for a brief period of time. After the brief period of time, the drive mechanism 12 may be directed to reverse at a slow speed in order to unwind energy that is stored in the drive mechanism 12. In some cases, torque thresholds may be set based at least in part upon how fast the operator is running the device. In some instances, torque thresholds may be set based at least in part on how quickly the torque is increasing, and/or other operational parameters.

Figure 2:
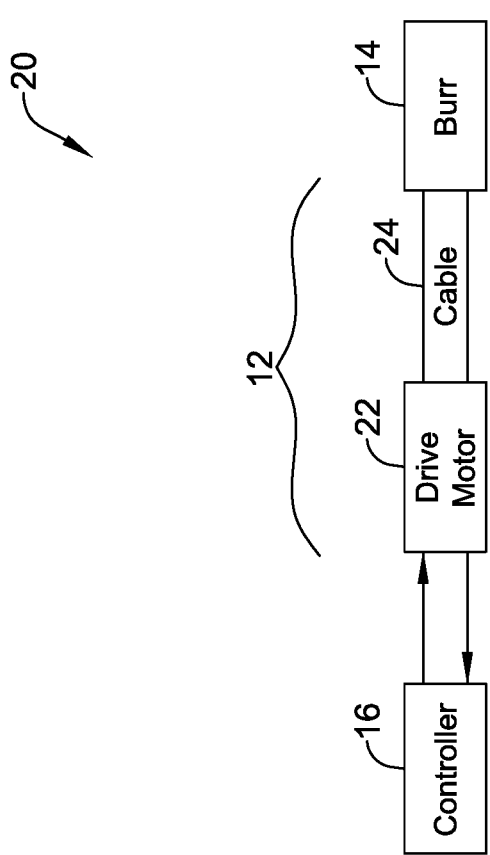
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some cases, features of the atherectomy system 20 may be combined with features of the atherectomy system 10. In some cases, the atherectomy system 20 may also include a handle (not shown).

Figure 3:
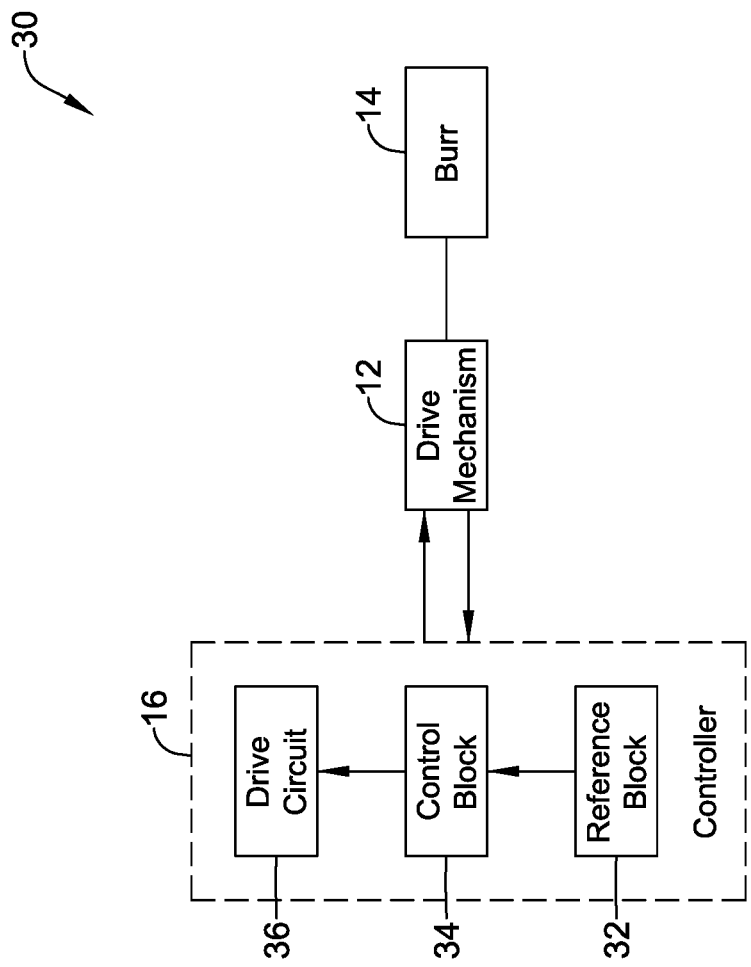
FIG. 3 is a schematic block diagram of an example atherectomy system.

FIG. 3 is a schematic block diagram of an example atherectomy system 30 in which the controller 16 includes a reference block 32, a control block 34 and a drive circuit 36. In some cases, features of the atherectomy system 30 may be combined with features of the atherectomy system 20 and/or the atherectomy system 10. In some cases, the reference block 32 may be adapted to receive a speed signal and to output a reference signal. In some cases, the reference block 32 may be adapted to output a reference signal that is either a nominal positive value, a small negative value or zero. In some cases, the reference block 32 may be adapted to default to the nominal positive value for the reference signal upon startup of the atherectomy system 10. In some cases, the reference block 32 may be adapted to add an offset value to the reference signal in order to accurately hold speed of the drive mechanism 12 during a no-load situation. Alternatively, the control block 34 may add the offset value to the reference signal.

The control block 34 may be adapted to receive the reference signal from the reference block 32 and to generate a resulting control effort signal. In some cases, the control block 34 includes a Proportional controller. In some instances, the control block 34 includes a Proportional Integral Derivative (PID) controller. The drive circuit 36 may be adapted to receive the control effort signal from the control block 34 and to regulate operation of the drive mechanism 12 accordingly.

Figure 4:
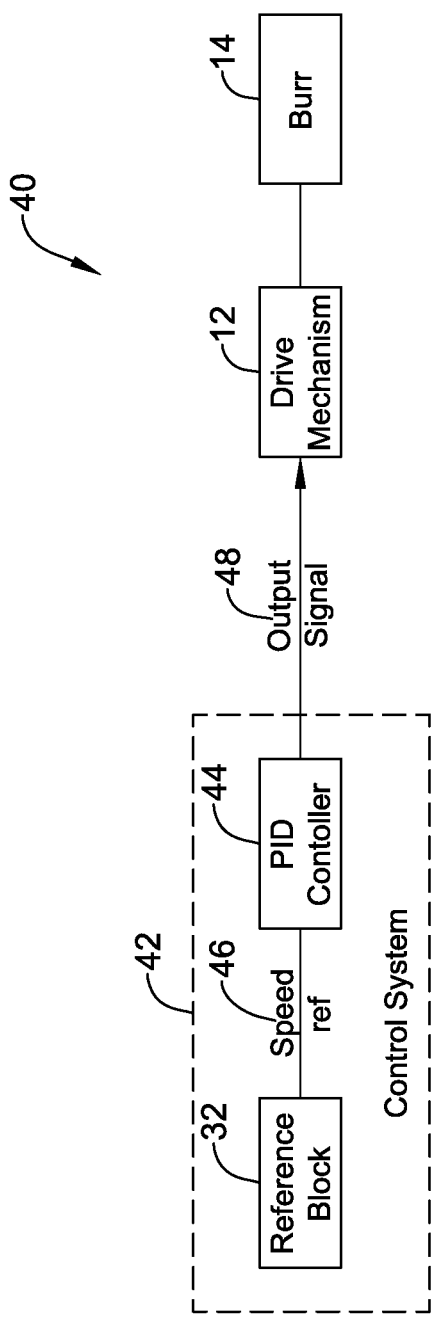
FIG. 4 is a schematic block diagram of an example atherectomy system.

FIG. 4 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10, the atherectomy system 20 or the atherectomy system 30. The control system 42 may include the reference block 32 as well as a Proportional Integral Derivative (PID) controller 44 that is operably coupled to the reference block 32. In some cases, the reference block 32 may determine a speed reference 46 that is selectable between a nominal value, a negative value and zero. In some instances, the PID controller 44 may be further adapted to add an offset value to the speed reference 46 received from the reference block 32, although in some cases, the reference block 32 may add the offset value. The PID controller 44 may be further adapted to provide a reduction in motor speed of the drive mechanism 12 that is greater than what would otherwise normally occur in response to an increasing torque experienced at the atherectomy burr 14.

The PID controller 44 may be adapted to utilize the speed reference 46, a Proportional (P) gain value, an Integral (I) gain value and a Derivative (D) gain value in determining an output signal 48 for the drive mechanism 12. In some cases, the drive mechanism 12 may include a drive motor and drive cable extending between the drive motor and the atherectomy burr 14. In some cases, the I gain value and the D gain value may be set to zero or to essentially about zero, meaning that the I and D values have little or no impact on control. In some cases, the P gain value is set to a low value that is non-zero, and permits a motor speed that is within about 90 percent of a reference speed.

In some cases, having a small P gain value enables the speed to drop considerably in response to a relatively minor increase in torque because with a small gain, a larger error signal (difference between reference speed and actual speed) will be needed to increase the commanded torque a given amount. As a result, increases in torque are easily communicated to a user of the atherectomy system 40. In some cases, this results in a small increase in torque causing a relatively large reduction in speed, which serves to alert the user to an increased torque situation. As a non-limiting example, perhaps a 5 or 10 percent increase in torque may result in a 20 to 30 percent, or a 20 to 40 percent, or a 20 to 50 percent decrease in speed. This also, in some cases, causes changes in torque command to be relatively slow, which in turn facilitates monitoring for a stuck atherectomy burr 14 condition.

In some cases, in response to an increasing torque as a result of the atherectomy burr 14 being stuck, the PID controller 44 may be adapted to increase torque until a predetermined threshold is reached. The reference block 32 may be adapted to subsequently set the speed reference 46 to the negative value for a period of time in order allow energy stored in the drive mechanism to unwind. This may be a period of 1 to 10 seconds, or 1 to 20 seconds, or longer, for example. In some cases, this can facilitate extraction of the atherectomy burr 14.

Figure 5:
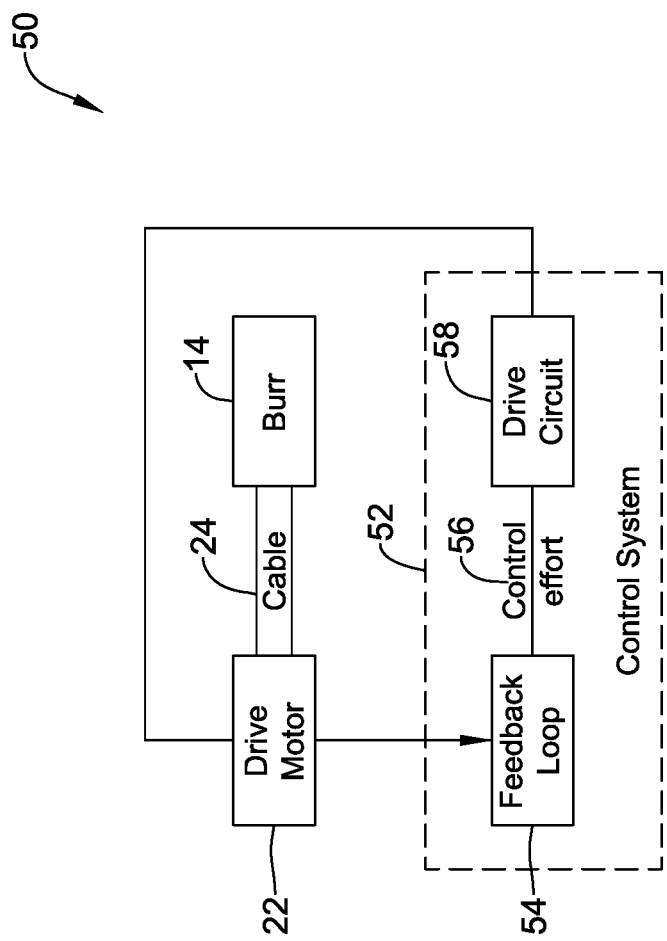
FIG. 5 is a schematic block diagram of an example atherectomy system.

FIG. 5 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20, the atherectomy system 30 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56. In some cases, the control system 52 may be further adapted to provide a reduction in motor speed of the drive motor 22 that is greater than what would otherwise normally occur in response to an increasing torque experienced at the atherectomy burr 14.

In some cases, the feedback loop 54 may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation. In some instances, for example if the atherectomy burr 14 becomes stuck, the control system 52 may be further adapted to increase the torque provided by the drive motor 22 until a torque threshold is reached for a brief period of time, and to subsequently direct the drive motor 22 to reverse at a slow speed in order to unwind energy in the drive mechanism.

Figure 6:
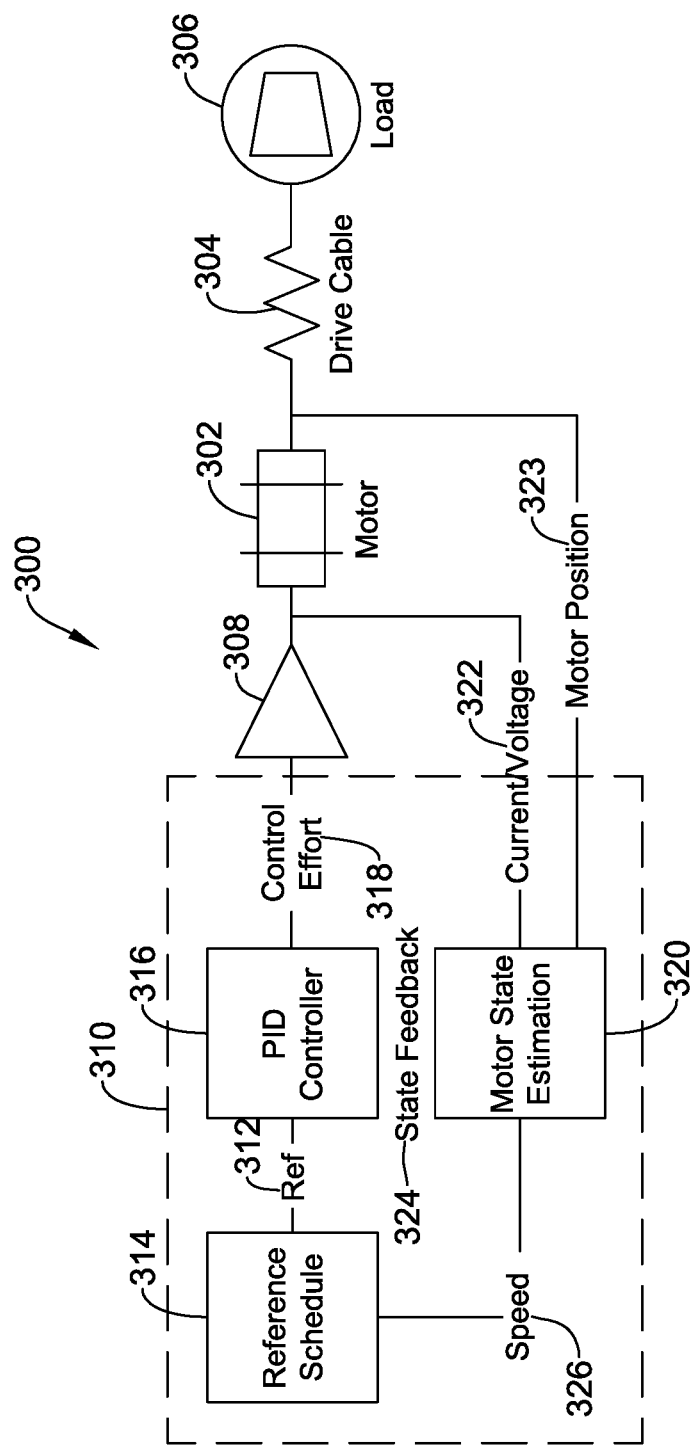
FIG. 6 is a schematic block diagram of an example atherectomy system.

FIG. 6 is a schematic block diagram of an example atherectomy system 300. In some cases, the atherectomy system 300 may be considered as being an example of the atherectomy system 10, 20, 30, 40 or 50. In some instances, features of the atherectomy system 300 may be combined with features of any of the atherectomy systems 10, 20, 30, 40 or 50, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive module 22 and/or the control system 106, for example.

The drive circuitry 308 receives an input from a feedback portion 310. In some cases, the feedback portion 310 begins with a reference input 312 from a reference schedule block 314, which provides the reference input 312 to a PID controller 316. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. A PID controller is a controller that includes a (P) proportional portion, an (I) integral portion and a (D) derivative portion. The PID controller 316 outputs a control effort value 318 to the drive circuitry 308. A motor state estimation block 320 receives a current/voltage signal 322 and a motor position signal 323 from the drive circuitry 308 and receives state feedback 324 from the PID controller 316. The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

Figure 7:
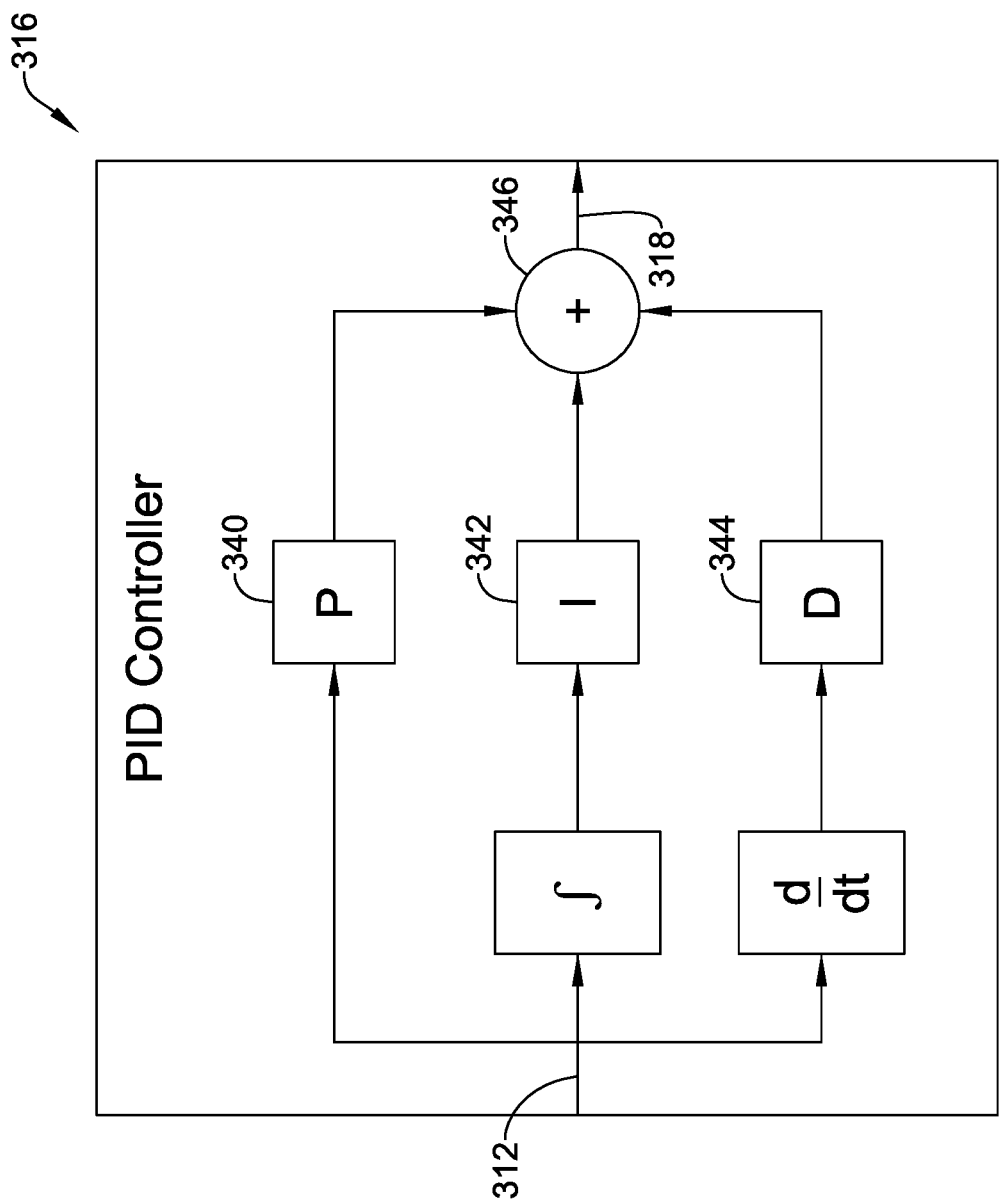
FIG. 7 is a schematic diagram of an example PID controller usable in the example atherectomy systems of FIGS. 1 through 6.

FIG. 7 is a schematic block diagram of the PID controller 316, which may be considered as being an example of the PID controller 44 shown in FIG. 4. A reference signal 312, which is representative of an error between a desired value and an actual value, enters the PID controller 316. The PID controller 316 calculates a P term 340, which is proportional to the error. The PID controller 316 calculates an I term 342, which is an integral of the error and a D term 344, which is a derivative of the error. These terms are added together at a summation point 346, resulting in an output of the control effort signal 318.

Figure 8:
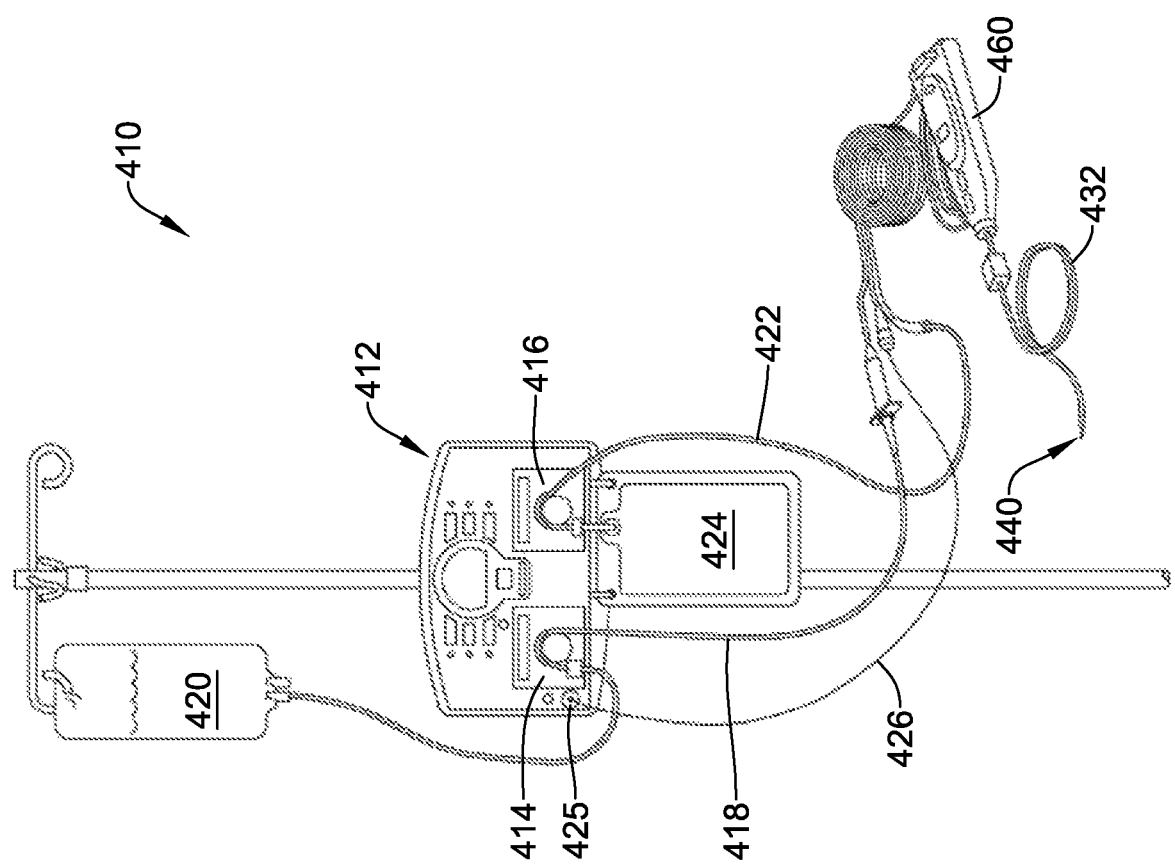
FIG. 8 is a schematic diagram of an example atherectomy system that may utilize the atherectomy control systems described with respect to FIGS. 1 through 6.

FIG. 8 illustrates an exemplary example of an interventional catheter assembly 410 with which the atherectomy systems 10, 20, 30, 40, 50 and 300 may be used. The interventional catheter assembly 410 includes a console unit 412, a controller 460, and a catheter system 432 having an operating head 440 located at or in proximity to the distal end of the catheter system. The controller 460 may be used to manipulate (e.g. advance and/or rotate) the catheter system 432 and operating head 440, or alternative controls may be provided. It will be appreciated that at least some of the functionality of the controller 460 and/or the console unit 412 may instead be incorporated into the atherectomy systems 10, 20, 30, 40, 50 and 300.

The console unit 412 incorporates an infusion pump 414 and an aspiration pump 416. During operation of the interventional catheter, an infusate conduit 418 draws fluid from an infusate reservoir 420 and operably contacts the infusion pump 414 to provide fluid through an infusion lumen in catheter system 432 to one or more infusion ports provided in proximity to the operating head. Similarly but in reverse, fluids with entrained particulates are withdrawn from the site of intervention through an aspiration lumen in the catheter system 432 and conveyed to an aspiration conduit 422, which is in operable contact with the aspiration pump 416, and communicates with the aspirate collection vessel 424. The console unit 412 may also provide a power source for operating the operating head and system components, or it may be in communication with an external power source. In some cases, the console unit 412 may provide power to the interventional catheter assembly and the controller 460 via a device power port 425 and power cord 426.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 412. The console unit 412 is generally provided as a reusable assembly and is generally operated outside the sterile field. It may be mountable on a portable stand to facilitate convenient placement during interventions.

One function of the console unit 412 is to provide feedback of system and/or environmental conditions or operating parameters. The console unit may output operational information concerning operating conditions and feedback from the material removal site to the operator. In some cases, the console unit 412 may provide continuously updated output to an operator of operating parameters such as operating head rotation rate, which may include the actual run speed as well as the desired speed; operating head advance rate; aspiration rate and/or volume; infusion rate and/or volume; length of the body or matter to be removed that is traversed; and the like.

Certain automated and selectable control features may be implemented in the console unit 412. Preset routines or programs involving various operating parameters may be preselected, stored and selectable by an operator, for example. Thus, in some cases, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

In some cases, aspiration may be included in the interventional catheter systems disclosed herein. In certain cases, fluid and associated particulates are aspirated from the intervention site at rates of at least 5 ml/min and, in many cases, fluid and associated particulates may be aspirated at rates of at least 15 ml/min, or at least 25 ml/min. In exemplary interventional catheter systems, the aspiration site may be more than a meter away from the controller 460 through an aspirate removal passageway located within the catheter system 432 and having a diameter of less than 0.10 inch, for example between about 0.050 to 0.070 inch. The distance that the aspirate travels between controller 460 and console unit 412 may be from about ½ meter to several meters, through an aspirate conduit that is between about 0.015 to about 1.0 inch in diameter. The blood and debris being aspirated are relatively viscous fluids, and achieving a relatively constant and high level of aspiration under these conditions is essential.

In one case, aspiration pump 416 may be a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 424 and a sealed aspiration conduit may be provided as part of a sterile disposable interventional catheter kit. A distal end of the aspiration conduit may be pre-mounted on and sealed to the controller 460. A proximal portion of the aspiration conduit is mounted on the aspiration pump prior to operation of the interventional catheter and the aspirate collection bag is mounted to or in proximity to the control module.

The infusion pump 414 may also be a multi-lobed roller pump employing variable or selectable rotation rates to control the infusion rate and volume. A simple bag or another infusate reservoir, such as those used for intravenous infusions, may be used to supply the infusate. For example, an infusate reservoir 420 having a sealed conduit that is mounted in the infusion pump 416 during operation of the interventional catheter may be provided. In some cases, the sealed infusate conduit may be provided as part of the sterile disposable interventional catheter system and a distal end of the infusate conduit may be pre-mounted on and sealed to the controller 460. A proximal portion of the infusate conduit may be connected to an infusate reservoir, such as a saline bag, and mounted in proximity to the infusion pump prior to operation. A control feature that automatically disables the infusion pump and/or power to the operating head may be activated upon detection of a fault (e.g. a bubble) in the infusate conduit.

The console unit 412 may also have control switches for activating and shutting down the aspiration pump and system, and for activating and shutting down the infusion pump and system. These control features may be provided as simple on/off switches. Alternatively, systems providing different levels or rates of aspiration and/or infusion that are selectable by an operator may be provided. In addition, the console unit 412 may be provided with a timing mechanism that determines, and displays, the elapsed time of operation of the operating pressure and/or the aspiration and infusion systems. The volumes of aspirate withdrawn and the volume of infusate introduced may also be detected and displayed by the console unit 412. Detection systems for monitoring the levels of aspirate and infusate in the respective reservoirs may be incorporated and alarms indicating an overfill condition for the aspirate collection system or a low supply condition for the infusate reservoir may be provided. Backup aspirate collection and infusate supply systems may also be provided.

In some cases, the console unit 412, together with the aspiration pump 416, the infusion pump 414 and the associated control and display features, may be provided as a separate, re-usable unit, that may be used as standard equipment in operating rooms, for example. In the system illustrated, the console unit 412 is not contaminated by contact with blood or aspirate during operation, and the power and control systems are durable and long-lasting and may be reused for many interventions. The console unit 412 may be provided in a housing designed to sit on a platform during operation, or the housing may be designed for mounting on a portable structure, such as an i.v. pole or another structure, or may be a self-contained free-standing portable structure. The interventional catheter system, including the catheter system 432 with the operating head 440, the controller 460, the aspirate conduit 422, the aspirate collection vessel 424, and the infusate conduit 418 may be provided as a sterile, single use system kit.

The controller 460, which may be constructed from a durable, sterilizable material, such as hard plastic, may be provided in any convenient ergonomic design and constructed for placement in proximity to and/or in contact with the external body. In one instance, the controller may include an integrated handle for operator convenience in holding and supporting the controller during operation. The catheter system 432, exiting the controller 460, may be axially translatable with respect to the controller 460 as the operating head and catheter system are guided to a target material removal site. It will be appreciated that some of the control and operational features described herein with reference to the controller 460 may be provided in the console unit 412 and, likewise, some of the control and operational features described with reference to the console unit 412 may be provided in the controller 460.

Figure 9:
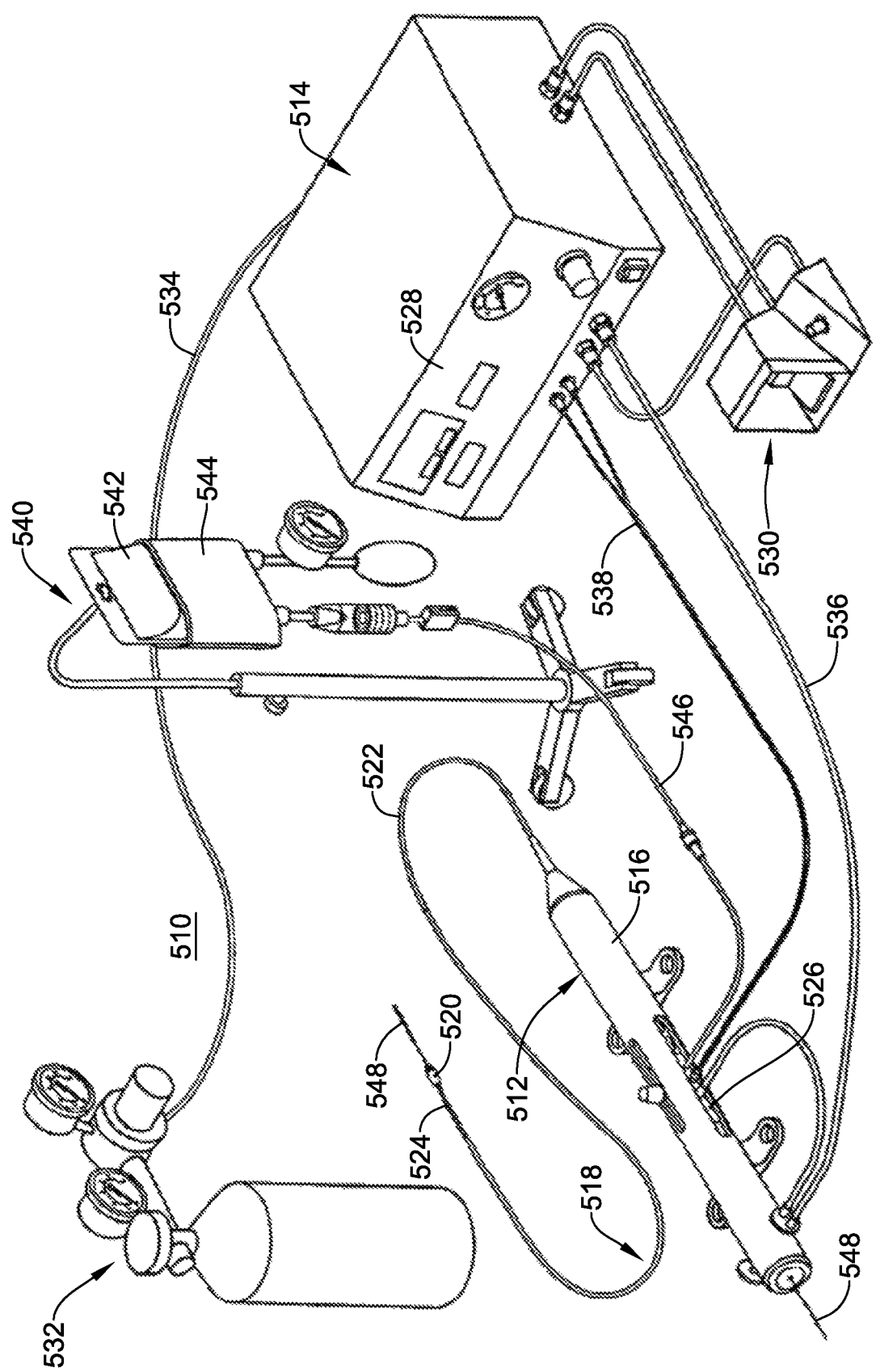
FIG. 9 is a schematic diagram of an example atherectomy system that may utilize the atherectomy control systems described with respect to FIGS. 1 through 6.

FIG. 9 shows an example rotational atherectomy system 510 with which the atherectomy systems 10, 20, 30, 40, 50 and 300 may be used. The rotational atherectomy system 510 may include a rotational atherectomy device 512 and a controller 514 for controlling the rotational atherectomy device 512. The rotational atherectomy device 512 may include a housing 516 and an elongate shaft 518 extending distally from the housing 516 to a cutting member 520 located at a distal end of the elongate shaft 518. The elongate shaft 518 may include a drive shaft 524 to provide rotational motion to the cutting member 520. In some instances, the elongate shaft 518 may include an outer tubular member 522 having a lumen extending therethrough and the drive shaft 524 may extend through the lumen of the outer tubular member 522. The drive shaft 524, which may be fixed to the cutting member 520, may be rotatable relative to the outer tubular member 522 to rotate the cutting member 520. In some instances the axial position of the cutting member 520 relative to the outer tubular member 522 may be adjusted by moving the drive shaft 524 longitudinally relative to the outer tubular member 522. For example, the atherectomy device 512 may include an advancer assembly 526 positioned in the housing 516, or otherwise provided with the housing 516, that is longitudinally movable relative to the housing 516. The outer tubular member 522 may be coupled to the housing 516 while the drive shaft 524 may be coupled to the advancer assembly 526. Accordingly, the drive shaft 524 (and thus the cutting member 520) may be longitudinally movable relative to the outer tubular member 522 by actuating the advancer assembly 526 relative to the housing 516.

The rotational atherectomy device 512 may include a prime mover (not shown) to provide rotational motion to the drive shaft 524 to rotate the cutting member 520. For example, in some instances the prime mover may be a fluid turbine within the housing 516, such as provided with the advancer assembly 526. In other instances, however, the prime mover may be an electrical motor, or the like. The controller 514 may be used to control the prime mover. For example, the user may provide power to the prime mover and/or control the speed of rotation of the drive shaft 524 via the controller 514. For example, the front panel 528 of the controller 514 may include a user interface including a power switch, speed control mechanism (e.g., a speed control knob and/or buttons), a display, and/or other features for controlling the rotational atherectomy device 512. In some instances, the rotational atherectomy system 510 may include a remote control device 530, such as a foot pedal, a hand control, or other mechanism which may be used to control the power and/or speed to the prime mover, for example.

In instances in which the prime mover is an electric motor, the electric motor may be coupled to the controller 514 via an electrical connection to control the electric motor and/or provide electricity to the electric motor.

In some instances, the rotational atherectomy device 512 may include a speed sensor, such as an optical speed sensor, coupled to the controller 514 via a connector 538, such as a fiber optic connector to provide speed data to the controller 514. In other instances, an electronic sensor, such as a Hall Effect sensor, or other type of sensor may be used to sense the speed of the drive shaft 524 and cutting member 520. The speed data may be displayed, such as on the front panel 528 and/or the controller 514, and/or used to control the speed of the cutting member 520, such as maintaining a desired speed of the cutting member 520 during a medical procedure.

In some instances, the rotational atherectomy system 510 may be configured to infuse fluid through the elongate shaft 518 to the treatment site and/or aspirate fluid through the elongate shaft 518 from the treatment site. For example, the rotational atherectomy system 510 may include a fluid supply 540 for providing a flow of fluid through a lumen of the elongate shaft 518 to a treatment site. In some instances the fluid supply 540 may include a saline bag 542 which may be pressurized by a pressure cuff 544 to provide a pressurized fluid (e.g., saline) to the rotational atherectomy device 512 through a fluid supply line 546. In other instances, an infusion pump, such as a peristaltic pump, may be used to deliver pressurized fluid to the rotational atherectomy device 512. Additionally or alternatively, in some cases the rotational atherectomy system 510 may be configured to aspirate fluid from the treatment site. For example, the rotational atherectomy system 510 may include an aspiration pump, such as a peristaltic pump, to generate a vacuum to aspirate fluid through a lumen of the elongate shaft 518 to a fluid collection container (not shown), if desired.

In some instances, the elongate shaft 518 of the rotational atherectomy device 512 may be advanced over a guidewire 548 to a treatment site. For example, the drive shaft 524 may include a guidewire lumen through which the guidewire 548 may pass. Additionally or alternatively, the elongate shaft 518 may be advanced through a lumen of a guide catheter to a treatment site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
   a drive mechanism adapted to rotatably actuate an atherectomy burr, the drive mechanism comprising a drive cable coupled with the atherectomy burr and a drive motor adapted to rotate the drive cable in a rotational direction; and
   a control system adapted to regulate operation of the drive mechanism, the control system including:
   a reference circuit for determining a speed reference, the speed reference selectable between a nominal value, a negative value, and zero; and
   a Proportional Integral Derivative (PID) controller operably coupled to the reference circuit for receiving the speed reference, the PID controller adapted to utilize the speed reference, a Proportional (P) gain value, an Integral (I) gain value and a Derivative (D) gain value in determining an output signal for the drive mechanism;
   the PID controller further adapted to add an offset value to the speed reference received from the reference circuit;

wherein the PID controller is further adapted to command a reduction in motor speed of the drive mechanism, while still driving the drive mechanism in the rotational direction, that is greater than what would otherwise normally occur in response to an increasing torque experienced at the atherectomy burr; and wherein the PID controller is further adapted to, in response to an increasing torque as a result of a stuck atherectomy burr, increase torque until a predetermined threshold is reached; and the reference circuit is adapted to set the speed reference to the negative value in order to unwind energy stored in the drive mechanism.

2. The atherectomy system of claim 1, wherein the I gain value and the D gain value are set to zero or about zero.

3. The atherectomy system of claim 1, wherein the P gain value is set to a low value.

\* \* \* \* \*